United States Patent [19]

Plapp et al.

[11] Patent Number: 4,482,568

[45] Date of Patent: Nov. 13, 1984

[54] INHIBITION OF ALCOHOL METABOLISM BY TETRAMETHYLENE SULFOXIDES

[75] Inventors: Bryce V. Plapp, Iowa City; Vijay K. Chadha, Coralville, both of Iowa

[73] Assignee: University of Iowa Research Foundation, Iowa City, Iowa

[21] Appl. No.: 542,482

[22] Filed: Oct. 17, 1983

[51] Int. Cl.$^3$ .................... A61K 31/38; C07D 333/00
[52] U.S. Cl. ...................................... 424/275; 549/29
[58] Field of Search .................... 549/29, 87; 424/275

[56] References Cited

U.S. PATENT DOCUMENTS

| | | |
|---|---|---|
| 2,563,073 | 8/1951 | Schmerline . |
| 2,613,214 | 10/1952 | Pines . |
| 2,625,553 | 1/1953 | Pines et al. . |
| 3,056,793 | 10/1962 | Luvisi . |
| 3,151,140 | 9/1964 | Hubal et al. . |
| 3,408,358 | 10/1968 | Hardtmann et al. . |
| 3,862,174 | 1/1975 | Mizutani et al. . |
| 3,969,358 | 7/1976 | Anselem . |
| 4,116,975 | 9/1978 | Klaus et al. . |

OTHER PUBLICATIONS

Chem. Abst., vol. 78, 130174f.
Sharkawi, N., (1979), Toxicology Letters 4, 493–497.
Zaiken, V. G., Trusora, E. A. and Shcherbakova, L. P. (1978), Khimiya Geterotsiklicheskikh Soedinenii, No. 2, pp. 176–181, Feb. 1978, [Plenum Press translation UDC 543.51:527.732'818, pp. 135–140].

Primary Examiner—Alan Siegel
Attorney, Agent, or Firm—Zarley, McKee, Thomte, Voorhees & Sease

[57] ABSTRACT

Tetramethylene sulfoxide and its substituted derivatives have been found to be exceptionally potent inhibitors of oxidation of alcohols by liver alcohol dehydrogenases.

16 Claims, 1 Drawing Figure

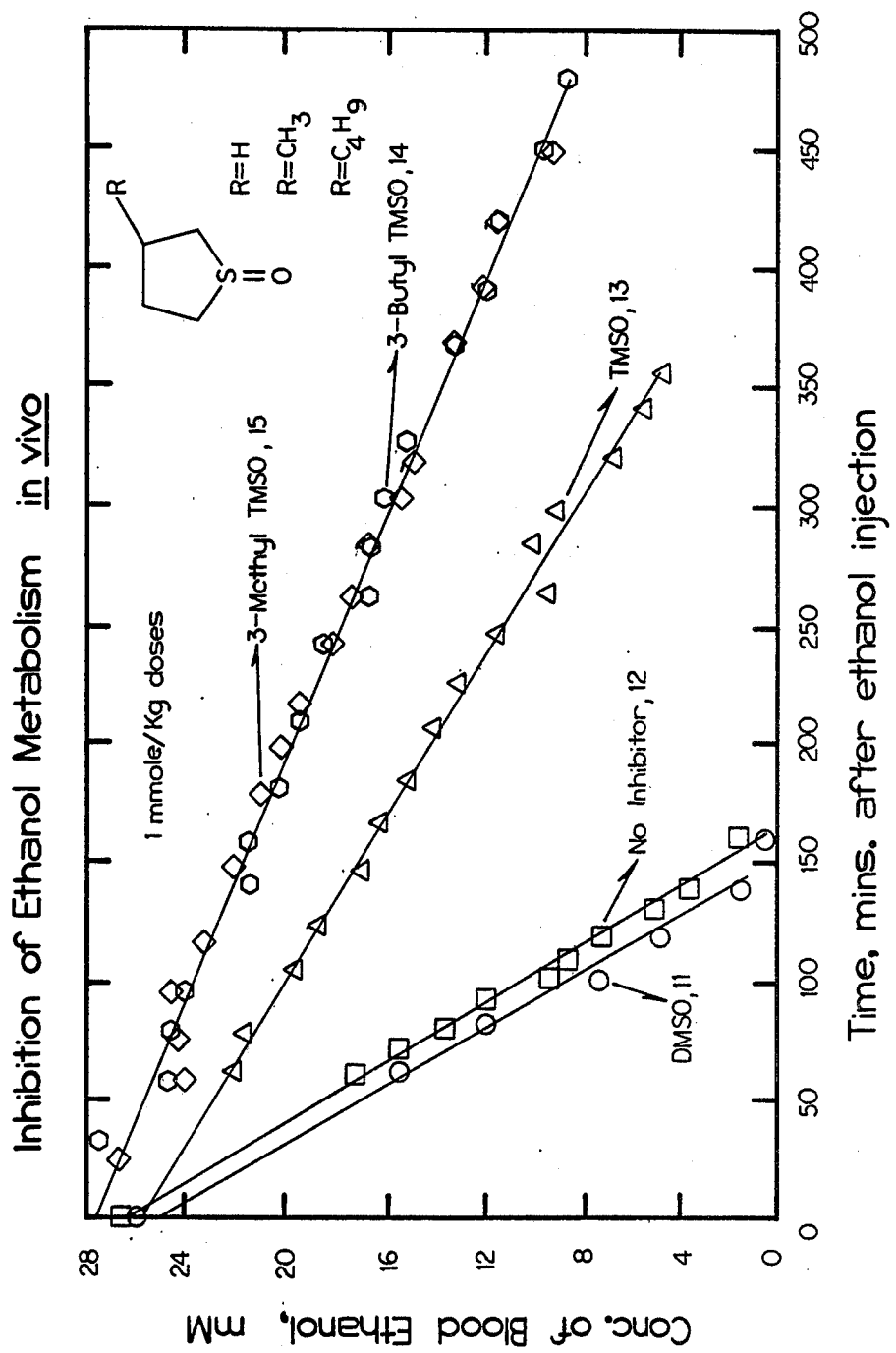

ns by tetramethylene sulfoxides

GRANT REFERENCE

This invention was conceived and developed in part with funds from a National Institute of Alcohol Abuse and Alcoholism Grant, No. AA 00279.

BACKGROUND OF THE INVENTION

There is a continuing need for effective alcohol metabolism inhibitors. This is so because some common alcohols, when ingested, are toxic. For example, methanol (wood alcohol), isopropyl alcohol (rubbing alcohol), and ethylene glycol (anti-freeze), are all toxic. When these compounds are ingested and metabolized in the liver, by liver alcohol dehydrogenases, the metabolic process first forms corresponding carbonyl compounds such as aldehydes, followed by further metabolism. For example, methanol is metabolized in the liver first to formaldehyde, then to formic acid. The increased acid content of the blood results in a lowering of the pH, which can be lethal. Accordingly, there is a real and continuing need for the development of alcohol metabolism inhibitors.

The function of the inhibitor is to prevent the ingested alcohol from being metabolized by alcohol dehydrogenases in the liver. If the ingested alcohol is prevented from being metabolized, eventually the alcohol will be excreted through the breath and the urine over a two to three day period. Since the harmful metabolic products are not formed, there is no significant toxicity to the organism.

The currently known treatments for ingestion of toxic alcohols include saturation of the organism with ethanol, the theory being that ethanol is a competitive inhibitor, and will be preferentially metabolized by the alcohol dehydrogenases in the liver, resulting in less metabolism of the ingested, toxic alcohol. The disadvantages of the use of ethyl alcohol for such treatments are, of course, that it is a depressant, that it is not a very effective inhibitor, and that it is only a competitive inhibitor.

There is therefore, a real and continuing need for inhibitors known as uncompetitive or noncompetitive inhibitors. These terms refer to an inhibitor compound whose effect cannot be reversed by the substrate (alcohol) during the metabolic oxidation process. There are, for example, certain amide compounds which are known to be uncompetitive inhibitors, see Sharkawi, M., *Toxicology Letters*, 1979, 4, 493-497. In addition, some slight inhibitory effect has been reported with dimethyl sulfoxide in the same article. However, surprisingly, the compounds of this invention are uncompetitive inhibitors which are as much as one thousand-fold more effective than dimethyl sulfoxide. Such a dramatic increase in uncompetitive inhibition properties would not be predicted from the properties of dimethylsulfoxide.

Accordingly, it is the primary objective of the present invention is to develop truly useful uncompetitive or non-competitive inhibitors of the metabolism of alcohols.

It is another objective of the present invention to develop significant and effective alcohol metabolism inhibitors from tetramethylene sulfoxide and its three position substituted derivatives.

Another primary objective of the present invention is to develop certain novel substituted tetramethylene sulfoxide derivatives which, because of their potency and uncompetitive nature, are especially effective in inhibiting alcohol metabolism in animals.

Yet another objective of the present invention is to develop potent and uncompetitive alcohol metabolism inhibitors which are useful for the treatment of poisoning by methanol and ethylene glycol.

A further objective of the present invention is to prepare pharmaceutical compositions containing tetramethylene sulfoxide, or substituted tetramethylene sulfoxides, for use as inhibitors of the metabolism of alcohols.

SUMMARY OF THE INVENTION

Uncompetitive alcohol inhibitor compositions for warm blooded animals are prepared containing a small, but therapeutically effective dosage of tetramethylene sulfoxide, or, preferably 3-substituted tetramethylene sulfoxides. There can be no carbon chain substitutions on the two position.

BRIEF DESCRIPTION OF THE DRAWINGS

FIG. 1 shows a graph illustrating the effectiveness of the compounds of this invention as uncompetitive alcohol metabolism inhibitors, in comparison with dimethylsulfoxide (DMSO), and without use of any inhibitor.

DETAILED DESCRIPTION OF THE INVENTION

This invention relates to the discovery and preparation of organic compounds that are potent inhibitors of alcohol metabolism. Tetramethylene sulfoxide and its 3-substituted derivatives have been found to be exceptionally potent inhibitors of the oxidation of ethanol by isolated liver alcohol dehydrogenases, and to effectively inhibit ethanol metabolism in animals. 3-Substituted derivatives of tetramethylene sulfoxide have better inhibitory potency than the unsubstituted compound, and are therefore preferred. Based upon animal studies to date, it is reasonably expected that these compounds would be especially effective in inhibiting alcohol metabolism in higher animals including man. Thus, such compounds are useful for the treatment of poisoning by methanol and ethylene glycol in man, since the oxidation of these alcohols to toxic products by alcohol dehydrogenase in the liver would be prevented. If the oxidation of these alcohols is inhibited, it necessarily follows that the alcohols would be eliminated from the body by usual excretory processes.

The compounds useful for the treatment in this invention are tetramethylene sulfoxide and 3- or 3- and 4-substituted tetramethylene sulfoxides of the formula:

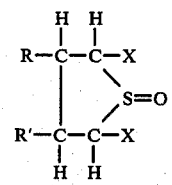

Where R and R' can be hydrogen, a hydrocarbyl radical, such as alkyl, aryl, alkaryl, aralkyl or cycloalkyl. Preferably R is $C_1$ to $C_8$, and R' hydrogen and most preferably, R is selected from the group consisting of methyl and butyl. X is hydrogen or fluoride, but preferably hydrogen.

The substituent in the 3-position increases the inhibitory potency by increasing the binding of the compound to the enzyme. The tighter the binding the better the inhibition. It is believed the same would be true for substitution of both 3- and the 4-positions. In contrast, substitution of carbon side chains at the 2-position will result in stereochemical hindrance, meaning that the inhibitor will not be as effective in binding to the liver enzyme alcohol dehydrogenase. The lack of effective binding means that the inhibitor would not function as well. While no side carbon chain may be at the 2-position, a small substitution, particularly fluorine, could improve the binding or prevent metabolism of the compound and thereby improve therapeutic utility.

It may also be possible, subject to further test confirmation, that bicyclic or tricyclic compounds, formed by substituents attached to carbons 2 and 3, or 3 and 4, or 2, 3, and 4, could also be inhibitors.

The dosage level of the tetramethylene sulfoxide compounds of this invention for effective therapeutic use as alcohol inhibitors will vary depending upon the body weight of the animal. Generally, however, a satisfactory dosage can be found at a dosage within the range of from about 2 micromoles per kilogram of body weight to about 100 micromoles per kilogram of body weight, preferably from 2 micromoles to about 20 micromoles per kilogram of body weight. Dosages within this range have not been found to have known harmful side effects.

Pharmaceutical carriers which are liquid or solid may be used. The preferred liquid carrier is an aqueous solution.

Solid pharmaceutical carriers such as starch, sugar, talc, mannitol and the like, may be used to form powders. Mannitol is the preferred solid carrier. The powders may be used as such for direct administration to a patient, or, instead, the powders may be added to suitable foods and liquids, including water, to facilitate administration. The powders also may be used to make tablets or to fill gelatin capsules. Suitable lubricants like magnesium sterate, binders such as gelatin, and disintegrating agents like sodium carbonate, in combination with citric acid, may be used to form the tablets.

Unit dosage form such as tablets and capsules may contain any suitable predetermined amount of one or more of the tetramethylene sulfoxides, and may be administered one or more at a time at regular intervals. Such unit dosage forms, however, should generally contain a concentration of from about 5% to about 20% by weight of one or more of the active tetramethylene sulfoxide compounds.

The oral route is preferred for administering the active tetramethylene sulfoxide inhibitors, although I.V. may work equally as well. Generally, the preferred dosages of from 2 micromoles per kilogram of body weight to 20 micromoles per kilogram of body weight, may be administered to obtain the stated activities, with the intake being three to four times per day over a three day period until all of the toxic alcohol is excreted.

Tetramethylene sulfoxide itself is a known compound and commercially available. 3-Methyltetramethylene sulfoxide (3-Methylthiolane-1-oxide) is believed to be a new compound. Likewise, 3-butyltetramethylene sulfoxide (3-butylthiolane-1-oxide) is believed to be a new compound. The synthesis for the active compounds of the previously described formula may be conveniently set forth by a flow diagram describing certain known synthesis procedures which are applied to preparation of the compounds of the present invention.

Chemical Synthesis

The preparation of the 3-butyltetramethylene sulfoxide is described by the following procedures:

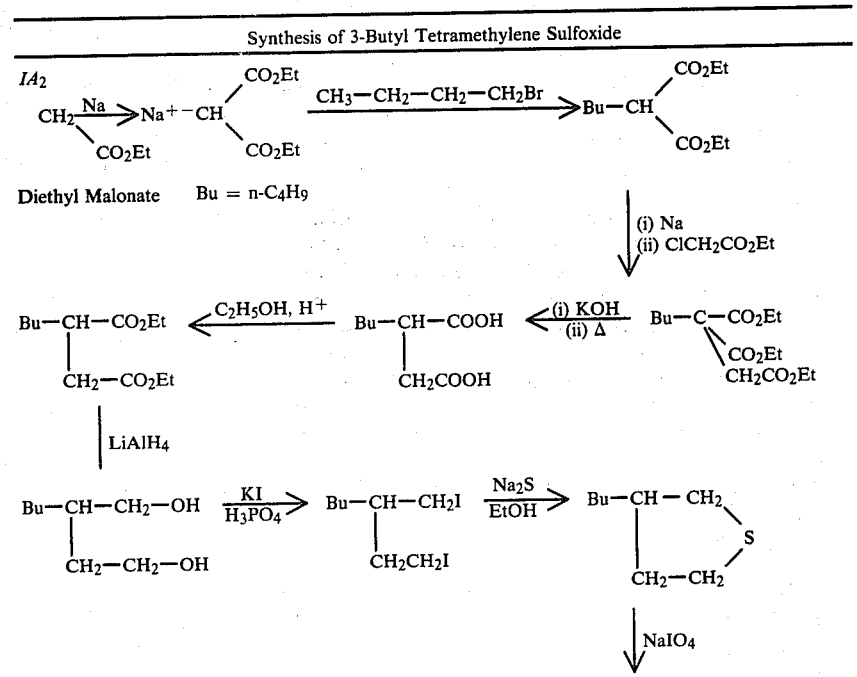

| Synthesis of 3-Butyl Tetramethylene Sulfoxide | |
|---|---|
| 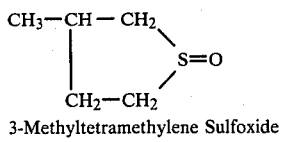<br>3-Methyltetramethylene Sulfoxide | 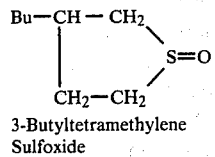<br>3-Butyltetramethylene Sulfoxide |

Briefly, a word description of this synthesis is set forth herein, with the details set forth in the examples. As can be seen in the schematic flow diagram, the synthesis involves activating the malonate ester by converting it to the sodium salt. The sodium salt is alkylated with, for example, butyl bromide. This in turn is followed by conventional potassium hydroxide hydrolysis. The hydrolysis is followed by decarboxylation and esterification. Thereafter, lithium aluminum hydride reduction will convert the esters to the alcohol, which is then converted to the iodide compound by reaction with potassium iodide in the presence of phosphoric acid. This in turn is followed by cyclization with sulfide to form the thioether (thiolane) precursor. The thioether is then oxidized in the presence of an oxidizing agent such as sodium meta periodate, to form the desired 3-substituted tetramethylene sulfoxide. Each of the steps are conventional and known synthesis techniques.

The following examples will show the preparation of 3-methyltetramethylene sulfoxide and 3-butyltetramethylene sulfoxide, as well as present biological data to show the effectiveness of the compounds.

EXAMPLES 3-methyl tetramethylene sulfoxide and 3-butyltetramethylene sulfoxide were prepared in accordance with the previously described synthesis scheme. In particular the steps were the following:

2-n-Butylsuccinic Acid. In a 500 ml three-necked flask fitted with a stirrer, 108 g (0.5 mole) of diethyl n-butylmalonate (Vogel, 1964; Aldrich Chemical Co.) was added dropwise to metallic sodium (13 g, 0.565 mole) in 200 ml of sodium-dried benzene over a period of about 45 min. To this gently refluxing suspension was added ethyl chloroacetate (65 g, 0.53 mole) slowly, and the reaction mixture was refluxed for 9–10 h. It was cooled, water was added, and the benzene layer separated. The aqueous layer was extracted 2–3 times with benzene and the combined extracts were dried over anhydrous MgSO$_4$. The solvent was removed by evaporation and the residue distilled under vacuum to give ethyl 2,2-dicarbethoxyheptanoate: bp. 120°–124°/0.7 mm, yield 117 g (76%).

The tricarboxylic ester (30 g, 0.1 mol) was added to potassium hydroxide (25.2 g, 0.45 mole) in an equal volume of water, and the reaction mixture was refluxed for 8 h. At the end of the reaction, most of the alcohol formed during reaction was removed by distillation. The residue was neutralized with concentrated hydrochloric acid and further heated at 130°–140° C. in an oil-bath for about 7 h (CO$_2$ evolution had ceased at this time). Water was added and the aqueous layer was extracted several times with ether. The combined extracts were dried over anhydrous MgSO$_4$ and the solvent was evaporated. The residual viscous liquid was triturated with a little ether and set aside until colorless crystals appeared: mp. 81°–82° (Lit. mp. 81°; Scheibler and Rettig, 1926).

Diethyl n-Butylsuccinate was prepared by refluxing the above acid (20.9 g, 0.12 mol) with 16.6 g of absolute alcohol in 50 ml of sodium-dried benzene and concentrated H$_2$SO$_4$ (4.3 ml) for 12 h. The reaction mixture was poured over 200 ml of water. The benzene layer was separated, washed with saturated sodium bicarbonate solution, once with water and dried over anhydrous MgSO$_4$. The benzene was evaporated and the residue distilled in vacuum: bp 88.5°–90°/0.6 mm, yield 23 g (83.3%). Anal. Calcd. for C$_{12}$H$_{22}$O$_4$; C, 62.58; H, 9.62. Found: C, 62.75; H, 9.63%.

2-n-Butyl-1,4-butanediol. In a 500 ml three-necked flask equipped with a stirrer and a dropping funnel, LiAlH$_4$ (4.6 g, 0.12 mole), and 150 ml of sodium-dried ether were stirred until most of the LiAlH$_4$ dissolved. A solution of diethyl n-butylsuccinate (23 g, 0.1 mole) in 75 ml of dry ether was added at such a rate that the ether refluxed gently. At the end of the addition, the reaction mixture was refluxed for 2 h. The excess of LiAlH$_4$ was decomposed by adding 13 ml of ethyl acetate slowly and with stirring. The reaction mixture was poured over 100 ml of 6N HCl. The mixture was transferred to a separatory funnel and the ether layer separated, washed once with water and dried over anhydrous MgSO$_4$. Ether was evaporated and the product was distilled under reduced pressure to give 12 g (82%) of the diol: b.p. 112°–114°/0.5 mm. Anal. Calcd. for C$_8$H$_{18}$O$_2$: C, 65.7; H, 12.40. Found: C, 65.64; H, 12.34%.

3-Butyltetramethylene sulfide. The 2-n-butyl-1,4-butanediol was converted into a 2-butyl-1,4-diiodobutane by the action of potassium iodide and polyphosphoric acid according to the procedure of Stone and Shechter (1963). The product was light brown (b.p. 105°–109°/0.35–0.4 mm) and was used for the preparation of the sulfide as follows: In a 500 ml three-necked flask, equipped with a stirrer, two dropping funnels and a condenser, 100 ml of 95% ethanol was placed and heated to reflux. In one dropping funnel was placed 2-butyl-1,4-diiodobutane (36.6 g, 0.1 mole) in 20 ml of ethanol and in the second funnel was placed 36 g (0.15 mole) of Na$_2$S.9H$_2$O in about 30 ml of hot water. The reagents were added at approximately the same rate (over 45–60 min) and the reaction mixture was refluxed further for 5–6 h. At the completion of the reaction, the mixture was distilled until no sulfide could be detected in the distillate. To this solution was added sufficient 5% aqueous HgCl$_2$ with stirring to obtain all of the sulfide as a white precipitate. The precipitate was collected by filtration and was subjected to steam distillation, until no more oily liquid distilled. The distillate was extracted with ether, and the extract was dried over KOH pellets. Diethyl ether was evaporated to give 6.5 g of the sulfide (45% yield). The NMR spectrum is consistent with the structure for 3-butyltetramethylene sulfide.

3-Methyltetramethylene sulfide. 2-Methyl-1,4-butanediol (Fluka) was converted into 2-methyl-1,4-diiodobutane and then to the 3-methyltetramethylene sulfide by following the above procedure. Yield 31%; b.p. 135°-136° (lit. b.p. 138.2; Whitehead et al., 1951). NMR (CDCl$_3$) δ 1.099 (d, 3H), 1.39-3.0 (m, 7H)

3-Butyltetramethylene sulfoxide. Sodium metaperiodate (4.1 g, 0.019 mole) was dissolved in 40 ml of water and cooled in an ice bath. 3-Butyltetramethylene sulfide (2.62 g, 0.018 mole) was added and the reaction mixture was stirred at 0° overnight. The NaIO$_3$ which precipitated during the reaction was removed by filtration, and the filtrate was extracted with two 40-ml portions of chloroform. The extract was dried over anhydrous MgSO$_4$, and the solvent was removed under reduced pressure. Vacuum distillation yielded 1.8 g (62%) of 3-butyltetramethylene sulfoxide: b.p. 95° C. C/0.52 mm. Anal. Calcd. for C$_8$H$_{16}$SO; C, 59.95, H, 10.06; S, 20.00. Found: C, 59.78; H, 10.05, S, 1972%. The NMR spectrum is consistent with the structure for 3-butyltetramethylene sulfoxide.

3-Methyltetramethylene sulfoxide. To a solution of NaIO$_4$ (13.2 g, 0.0616 mole) in 120 ml of water was added 3-methyltetramethylene sulfide (6.0 g, 0.0588 mole) and the reaction mixture was stirred overnight at 0° C. Following the procedure as described in the case of 3-butyltetramethylene sulfoxide yielded 3-methyltetramethylene sulfoxide: 3.5 g (51%), b.p. 96°-97°/10 mm. NMR (CDCl$_3$): 1.19 (t, 3H), 1.53-3.59 (m, 7H). Anal. Calcd. for C$_5$H$_{10}$SO.0.3 H$_2$O: C, 48.59; H, 8.64; S 25.94. Found. C, 48.97; H, 8.6; S 25.08%.

Other compounds in the series can be prepared by similar reactions. The 3-methyltetramethylene sulfoxide is prepared by a shorter route, since the 2-methyl-1,4-butanediol is commercially available. The parent compound, tetramethylene sulfoxide, is commercially available.

BIOLOGICAL EVALUATION

The following tests, both in vivo and in vitro, demonstrate the tremendous inhibitory effectiveness of the active compounds of this invention upon oxidation of alcohol by liver alcohol dehydrogenase in vitro or in animals.

The following table shows the results of studies on the inhibition of enzyme isolated from three different species and of ethanol metabolism in rats.

| | Inhibition of Alcohol Dehydrogenases And Ethanol Metabolism | | | | |
|---|---|---|---|---|---|
| | Liver Alcohol Dehydrogenase[a] | | | Ethanol (Elimination Rate) Metabolism In Rats[b] | |
| | In Vitro, K$_{ii}$, | | | | % |
| Compound | Horse | Monkey | Rat | K$_{ii}$ | Inhibition |
| Tetramethylene Sulfoxide | 19 | 1700 | 200 | 340 | 63 |
| 3-Methyltetramethylene sulfoxide | 7.5 | 450 | 18 | 150[c] | 72 |
| 3-Butyltetramethylene sulfoxide | 0.63 | 2.2 | 1.5 | 2--=0[c] | 76 |

[a]The K$_{ii}$ values (intercept) inhibition constants in micromolar units as determined against varied concentrations of ethanol as substrate. Purified or partially purified enzyme was tested under approximately physiological conditions, pH 7.3 and 37° C., except that the crystallized horse enzyme was tested at pH 7 and 25° C.
[b]The K$_{ii}$ (intercept inhibition constant, micromoles/kg) was determined with varied concentrations of inhibitor and ethanol by determination of blood alohol concentrations. For a survey of inhibitory potency, rats were given 19.6 mmoles of ethanol/kg body wt., i.p., and 1.0 mmole of the inhibitor, and the percentage inhibition of ethanol elimination was calculated with reference to an animal given no inhibitor. The maximum "inhibition" that can be obtained is about 85%, since some ethanol is eliminated by excretion, rather than by oxidation by alcohol dehydrogenase.
[c]The value was estimated from results from rats given 19.6 mmoles of ethanol/kg and 0.1, 0.4, and 1.0 mmoles/kg of the inhibitor.

The precise experimental details for assembling the data shown in the above table are reported in our *Journal of Medicinal Chemistry* article, 1983, Vol. 26, No. 6, at page 921. The entire article is incorporated herein by reference. In particular, for the rat studies, inhibition of ethanol metabolism by the active compounds of this invention were studied in vitro in liver alcohol dehydrogenase from horses, monkeys and rats. The in vivo study of ethanol metabolism in rats, and in particular its inhibition was studied with male Sprague-Dawley rats, which were given intraperitoneal injections of active compounds (0.1 molar) in saline at doses of 0.0, 0.25 and 0.5 or 1.0 mmole/kg of body weight. Ten minutes later, ethanol was injected intraperitoneally at a dose of 19.6 mmoles/kg of body weight. Blood samples were taken at intervals, timed from the ethanol injection, and analyzed by gas chromatography.

For the in vitro studies, the procedure was as follows:

Crystallized horse liver alcohol dehydrogenase was freed from endogenous ethanol by filtration though a column of Sephadex G-50. Inhibition studies were carried out with varied concentrations of ethanol (0.4–2 mM) at 1 mM NAD+ in 46 mM sodium phosphate buffer, pH 7, at 25° C. In each experiment, at least three different concentrations of inhibitor were tested and 32 initial velocities were determined (as in FIGS. 2A and 3A of the Journal article). Data for noncompetitive inhibition were fitted to the equation $v = VS/[K_m(1+1/K_{is})+S(1+1/K_{ii})]$, whereas the equation for uncompetitive inhibition has no $K_{is}$ term, and competitive inhibition has no $K_{ii}$ term. The equation giving the lowest standard errors and residual variance was concluded to give the best fit. Rat liver alcohol dehydrogenase was partially purified, and inhibition studies were performed as with the horse liver enzyme, except that the buffer was 83 mM potassium phosphate, pH 7.3, and 40 mM KCl, total ionic strength=0.25, and the temperature was 37.8° C. The concentration of NAD was 0.5 mM. These conditions are thought to resemble those found in vivo. The concentrations of ethanol were 0.4, 0.6, 1, and 2 mM, and the inhibitors were varied between 0 and 0.6 mM.

The above test results show the tremendous effectiveness of the inhibitors of this invention. Tetramethylene sulfoxides are exceptionally potent inhibitors of the alcohol dehydrogenase. For comparison, the inhibition constant for dimethyl sulfoxide with horse lever alcohol dehydrogenase is four to five mM.

The compounds are also potent inhibitors of ethanol metabolism in rats. The inhibitory potency in vivo parallels the potency in vitro, but the absolute magnitudes of the numbers differ, presumably because of distribution of the compounds in vivo.

As heretofore mentioned in the Sharkawi 1979 article, dimethyl sulfoxide has been reported to significantly "prolong the ethanol induced loss of righting reflex in mice". But the effects on ethanol elimination or specific alcohol metabolism were not shown. In order to compare dimethyl sulfoxide and its potential as an inhibitor with the compounds of this invention, rats were given dosages of 19.6 millimoles per kilogram of body weight of alcohol and/or injections of one millimole per kilogram of body weight of the inhibitors, either dimethyl sulfoxide, tetramethylene sulfoxide, 3-methyltetramethylene sulfoxide, or 3-butyltetramethylene sulfoxide. After injection, the alcohol concentration in the blood was measured. The drawing reports the alcohol concentration. The line designated by the numeral 12 represents ethanol without any inhibitor. The line designated by 11 represents ethanol with dimethyl sulfoxide. The line represented by the numeral 13 represents ethanol with tetramethylene sulfoxide. The remaining line represents both 3-methyltetramethylene sulfoxide 14 and 3-butyltetramethylene sulfoxide 15. It can be seen that in parallel studies at the same dosage levels, dimethyl sulfoxide is not effective as an inhibitor.

On the contrary, tetramethylene sulfoxide is far more effective and 3-methyltetramethylene sulfoxide and 3-butyltetramethylene sulfoxide are far superior to even tetramethylene sulfoxide. Thus, it can be seen that the compounds of the invention are demonstrated as potent and effective treatments for alcohol poisoning.

While heretofore the therapeutic application of the tetramethylene sulfoxides has been mentioned from time to time, in treating patients, it is believed that the administration of suitable doses would vary from one to six times per day over a period of a few days until the toxic alcohol was excreted. Since tetramethylene sulfoxides would also be eliminated as a function of time, repetitive doses are required.

What is claimed is:

1. A method of inhibiting alcohol metabolism in warm blooded animals comprising
treating the animal with a small but therapeutically effective dosage of a compound of the formula:

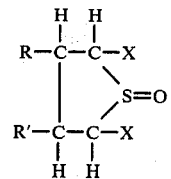

wherein R and R' are selected from the group consisting of hydrogen, alkyl, aryl, alkaryl, aralkyl, cycloalkyl, and X is selected from the group of hydrogen and fluoride.

2. A method of inhibiting alcohol metabolism in warm blooded animals comprising:
treating the animal with a small but therapeutically effective dosage of a compound of the formula

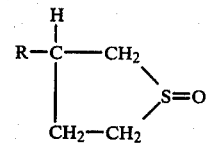

wherein R is selected from the group of hydrogen, alkyl, aryl, alkaryl, aralkyl and cycloalkyl.

3. The method of claim 2 wherein R is $C_1$ to $C_8$.
4. The method of claim 2 wherein R is hydrogen.
5. The method of claim 2 wherein R is methyl.
6. The method of claim 2 wherein R is butyl.
7. The method of claim 2 wherein the dosage is from about two micromoles to about 100 micromoles per kilogram of body weight.
8. The method of claim 7 wherein the dosage is from about two micromoles to about 20 micromoles per kilogram of body weight.
9. The method of claim 2 wherein the treatment with said dose is oral.
10. The method of claim 2 wherein the treatment with said dose is intravenous.
11. A unit dosage pharmaceutical composition for alcohol metabolism inhibition comprising a pharmaceutical carrier and a small but alcohol metabolism inhibiting effective amount of a compound of the formula:

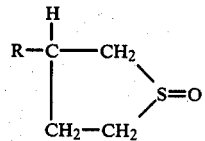

wherein R is selected from the group consisting of hydrogen, alkyl, aryl, alkaryl, aralkyl and cycloalkyl.

12. The composition of claim 11 wherein the dose is from about two miccromoles of said compound to about 20 micromoles of said compound per kilogram of body weight.
13. The composition of claim 11 wherein R is hydrogen.
14. The composition of claim 11 wherein R is $C_1$ to $C_8$ alkyl.
15. The composition of claim 11 wherein R is methyl.
16. The composition of claim 11 wherein R is butyl.

* * * * *